United States Patent [19]
Robinson et al.

[11] Patent Number: 5,643,578
[45] Date of Patent: Jul. 1, 1997

[54] IMMUNIZATION BY INOCULATION OF DNA TRANSCRIPTION UNIT

[75] Inventors: Harriet L. Robinson, Southboro; Ellen F. Fynan, Sterling, both of Mass.; Robert G. Webster, Memphis, Tenn.

[73] Assignees: University of Massachusetts Medical Center, Worcester, Mass.; St. Jude Children's Research Hospital, Memphis, Tenn.

[21] Appl. No.: 9,833

[22] Filed: Jan. 27, 1993

Related U.S. Application Data

[63] Continuation-in-part of Ser. No. 855,562, Mar. 23, 1992, abandoned.
[51] Int. Cl.$^6$ ............ A61K 39/145; A61K 39/00; C07H 21/04; C12N 15/11
[52] U.S. Cl. ............ 424/210.1; 424/209.1; 424/184.1; 536/23.1
[58] Field of Search ............ 424/89, 88, 209.1, 424/210.1, 184.1; 536/27, 23.1

[56] References Cited

U.S. PATENT DOCUMENTS 4,722,848  2/1988  Paoletti et al. ............ 424/89

FOREIGN PATENT DOCUMENTS

| | | |
|---|---|---|
| 0292879A3 | 11/1988 | European Pat. Off. . |
| 2166349 | 5/1986 | United Kingdom . |
| WO86/07593 | 12/1986 | WIPO . |
| WO89/07140 | 8/1989 | WIPO . |
| WO90/02797 | 3/1990 | WIPO . |
| WO90/02803 | 3/1990 | WIPO . |
| 9011092 | 10/1990 | WIPO ............ A61K 48/00 |
| WO92/01045 | 1/1992 | WIPO . |
| WO93/19183 | 9/1993 | WIPO . |

OTHER PUBLICATIONS

Nable, G.J. and Felgner, P.L., "Direct Gene Transfer For Immunotherapy and Immunization", *Trends in Biotechnology*, 11(5):211–215 (1993).

Francois-Loic Cosset, et al., "A New Avian Leukosis Virus-Based Packaging Cell Line that Uses Two Separate Transcomplementing Helper Genomes," *J. Virology* 64(3): 1070–1078 (1990).

Brown, W. David, et al., "Assessment of Retrovirus-Expressed Nucleoprotein as a Vaccine against Lethal Influenza Virus Infections of Chickens," *Avian Diseases* 36: 515–520 (1992).

Parker, S.E. et al., "Intramuscular Vaccination of Plasmid DNA Containing Viral Antigens Provides Protection Against a Lethal Viral Challenge," Abstracts of papers presented at the 1992 meeting on Modern Approaches To New Vaccines including Prevention of AIDS, Cold Spring Harbor Laboratory, New York, Sep. 16 –Sep. 20, 1992.

Rhodes, Gary H. et al., "Injection of Expression Vectors Containing Antigen Genes Induce Cellular and Humoral Immunity to the Antigen," Abstracts of papers presented at the 1992 meeting on Modern Approaches To New Vaccines including Prevention of AIDS, Cold Spring Harbor Laboratory, New York, Sep. 16 –Sep. 20, 1992.

Rhodes, Gary H. et al., "A Novel Method of Inducing Cellular and Humoral Immunity to HIV GP120 Protein by DNA Injection," Abstracts To New Vaccines including Prevention of AIDS, Cold Spring Harbor Laboratory, New York, Sep. 16 –Sep. 20, 1992.

Liu, M.A. et al., "Immunication with DNA Encoding a Consverved Internal Viral Protein Results in Protection from Morbidity and Mortality Due to Challenge with Influenza A in Mice," abstracts of papers presented at the 1992 meeting on Modern Approaches to New Vaccines Including Prevention of AIDS, Cold Spring Harbor Laboratory, New York, Sep. 16 –Sep. 20, 1992.

Wang, B. et al., "Genetic Immunization: A Novel Method for Vaccine Development Against HIV," Absracts of papers presented at the 1992 meeting on Modern Approaches To New Vaccines Including Prevention of AIDS, Cold Spring Harbor Laboratory, New York, Sep. 16 –Sep. 20, 1992.

Tang, De–Chu et al., "Genetic Immunization is a Simple Method for Eliciting an Immune Response," *Nature* 356: 152–154 (1992).

Hunt, Lawrence A. et al., "Retrovirus–Expressed Hemagglutinin Protects against Lethal Influenza Virus Infections," *Journal of Virology* 62 (8): 3014–3019 (1988).

Ulmer, Jeffrey B. et al., "Heterologous Protection Against Influenza by Injection of DNA Encoding a Viral Protein," *Science* 259: 1745–1749 (1993).

Webster, Robert G. et al., "Efficacy of Nucleoprotein and Haemagglutinin Antigens Expressed in Fowlpox Virus as Vaccine for Influenza in Chickens," *Vaccine* 9: 303–308 (1991).

Wolff, Jon A. et al., "Direct Gene Transfer into Mouse Muscle in Vivo," *Science* 247: 1465–1468 (1990).

Chambers, et al, 1988, "Protection of Chickens from . . ." Virology 167:414–421.

Huylebroeck, 1988, "Viral Delivery Systems for . . . " Technological Advances in Vaccine Dev. 84:279–293.

*Primary Examiner*—Lynette F. Smith
*Attorney, Agent, or Firm*—Hamilton, Brook, Smith & Reynolds, P.C.

[57] ABSTRACT

This invention relates to a method of immunizing a vertebrate, comprising introducing into the vertebrate a DNA transcription unit which comprises DNA encoding a desired antigen or antigens. The uptake of the DNA transcription unit by a host vertebrate results in the expression of the desired antigen or antigens, thereby eliciting humoral or cell-mediated immune responses or both humoral and cell-mediated responses. The elicited humoral and cell-mediated immune responses can provide protection against infection by pathogenic agents, provide an anti-tumor responses, or provide contraception. The host can be any vertebrate, avian or mammal, including humans.

19 Claims, 7 Drawing Sheets

SV40 Ori

CMV Pro

C

Intron pCMV pXF3

Rat Preproinsulin II Gene

Figure 4C

IMMUNIZATION BY INOCULATION OF DNA TRANSCRIPTION UNIT

RELATED APPLICATION

This Application is a Continuation-in-Part of U.S. application Ser. No. 07/855,562 filed Mar. 23, 1992, now abandoned, which is incorporated herein by reference.

GOVERNMENT SUPPORT

Work described herein was supported by U.S. Public Health Service Grants, Number RO1 CA 23086 and Number RO1 A1 08831. The U.S. Government has certain rights in this invention.

BACKGROUND OF THE INVENTION

Vaccination with inactivated or attenuated organisms or their products has been shown to be an effective method for increasing host resistance and ultimately has led to the eradication of certain common and serious infectious diseases. The use of vaccines is based on the stimulation of specific immune responses within a host or the transfer of preformed antibodies. The prevention of certain diseases, such as poliomyelitis, by vaccines represents one of immunology's greatest triumphs.

Effective vaccines have been developed for relatively few of the infectious agents that cause disease in domestic animals and man. This reflects technical problems associated with the growth and attenuation of virulent strains of pathogens. Recently effort has been placed on the development of subunit vaccines (vaccines that present only selected antigens from a pathogen to the host). Subunit vaccines have the potential for achieving high levels of protection in the virtual absence of side effects. Subunit vaccines also offer the opportunity for the development of vaccines that are stable, easy to administer, and sufficiently cost-effective for widespread distribution.

SUMMARY OF THE INVENTION

This invention relates to a method of immunizing an individual, comprising introducing into the individual a DNA transcription unit which comprises DNA encoding a desired antigen or antigens. The uptake of the DNA transcription unit by host cells results in the expression of the desired antigen or antigens, thereby eliciting humoral or cell-mediated immune responses or both humoral and cell-mediated responses. The elicited humoral and cell-mediated immune response can provide protection against infection by pathogenic agents, provide an anti-tumor response, or provide contraception. The host can be any vertebrate, avian or mammal, including humans.

The present invention relates in a particular embodiment to a method of immunizing an individual by contacting a mucosal surface in the individual with a DNA transcription unit capable of expressing a desired antigen or antigen.

The DNA transcription unit introduced by the present method can be used to express any antigen encoded by an infectious agent, such as a virus, a bacterium, a fungus, or a parasite, as well as antigenic fragments and peptides that have been experimentally determined to be effective in immunizing an individual against infection by a pathogenic agent. As stated above, DNA transcription units can also be used for contraceptive purposes or for anti-cancer therapy.

The desired antigen to be expressed can be designed so as to give internal, surface, secreted, or budding and assembled forms of the antigens being used as immunogens.

There are numerous advantages for the use of DNA for immunizations. For example, immunization can be accomplished for any antigen encoded by DNA. Furthermore, the DNA encoded antigens are expressed as "pure" antigens in their native states and have undergone normal host cell modifications. Also, DNA is easily and inexpensively manipulated and is stable as a dry product or in solution over a wide range of temperatures. Thus, this technology is valuable for the development of highly effective subunit vaccines.

BRIEF DESCRIPTION OF THE DRAWINGS

FIG. 4C is a schematic representation of the nonretroviral vector comprising a control DNA transcription unit, encoding no influenza virus antigens.

DETAILED DESCRIPTION OF THE INVENTION

Figure 1:
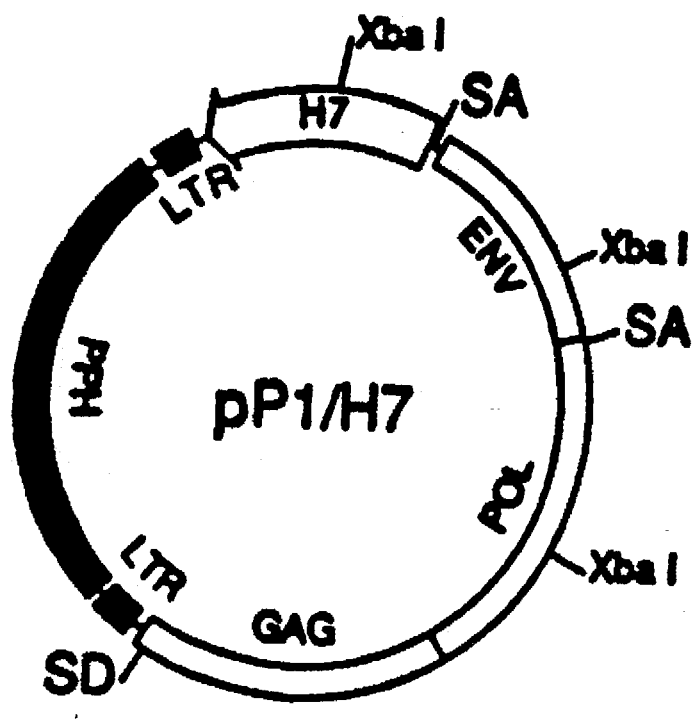
FIG. 1 is an illustration of a bacterial plasmid containing a DNA transcription unit (referred to as pP1/H7) comprising an influenza virus hemagglutinin type 7 (H7) gene expressed by a replication competent retroviral vector.

This invention relates to a method of immunizing vertebrates, particularly mammals, including humans, against a pathogen, or infectious agent, thereby eliciting humoral and/or cell-mediated immune responses which limit the spread or growth of the infectious agent and result in protection against subsequent challenge by the pathogen or infectious agent.

The term "immunizing" refers herein to the production of an immune response in a vertebrate which protects (partially or totally) from the manifestations of infection (i.e., disease) caused by an infectious agent. That is, a vertebrate immunized by the present invention will not be infected or will be infected to a lesser extent than would occur without immunization.

A DNA transcription unit is a polynucleotide sequence which includes at least two components: antigen-encoding DNA and transcriptional promoter elements. A DNA transcription unit may optionally include additional sequences, such as: enhancer elements, splicing signals, termination and polyadenylation signals, viral replicons and bacterial plasmid sequences.

The DNA transcription unit can be produced by a number of known methods. For example, using known methods, DNA encoding the desired antigen can be inserted into an expression vector to construct the DNA transcription unit. See Maniatis et al., *Molecular Cloning, A Laboratory Manual*, 2d, Cold Spring Harbor Laboratory Press (1989).

3

The DNA transcription unit can be administered to an individual, or inoculated, in the presence of adjuvants or other substances that have the capability of promoting DNA uptake or recruiting immune system cells to the site of the inoculation. It should be understood that the DNA transcription unit itself will be expressed by host cell factors.

The "desired antigen" can be any antigen expressed by an infectious agent or any antigen that has been determined to be capable of eliciting a protective response against an infectious agent. These antigens may or may not be structural components of the infectious agent. The encoded antigens can be translation products or polypeptides. The polypeptides can be of various lengths. They can undergo normal host cell modifications such as glycosylation, myristoylation or phosphorylation. In addition, they can be designed to undergo intracellular, extracellular or cell-surface expression. Furthermore, they can be designed to undergo assembly and release from cells.

Potential pathogens for which the DNA transcription unit can be used include DNA encoding antigens derived from any virus, chlamydia, mycoplasma, bacteria, parasite or fungi. Viruses include the herpesviruses orthomyxoviruses, rhinoviruses, picornaviruses, adenoviruses, paramyxoviruses, coronaviruses, rhabdoviruses, togaviruses, flaviviruses, bunyaviruses, rubella virus, reovirus, hepadna viruses and retroviruses including human immunodeficiency virus. Bacteria include mycobacteria, spirochetes, rickettsias, chlamydia, and mycoplasma. Fungi include yeasts and molds. Parasites include malaria. It is to be understood that this list does not include all potential pathogens against which a protective immune response can be generated according to the methods herein described.

An individual can be inoculated through any parenteral route. For example, an individual can be inoculated by intranasal, intravenous, intraperitoneal, intradermal, subcutaneous or intramuscular methods. In a particular embodiment of the present invention, an individual is vaccinated by contacting a mucosal surface on the individual with the desired DNA transcription unit in a physiologically compatible medium. The DNA transcription unit can be administered to a mucosal surface by a variety of methods, including DNA-containing nose-drops, inhalants and suppositories.

Any appropriate physiologically compatible medium, such as saline, is suitable for introducing the DNA transcription unit into an individual.

The following Examples describe vaccination trials using direct DNA inoculations designed for use in both avian and murine influenza virus models. Both of these models afford rapid assays for protective immunizations against lethal challenges, wherein challenge of an unimmunized animal causes death within 1–2 weeks.

Immunization as described herein has been accomplished with DNA transcription units (i.e., vectors) that express an influenza virus hemagglutinin glycoprotein. This protein mediates adsorption and penetration of virus and is a major target for neutralizing antibodies. Influenza virus hemagglutinin proteins have 14 different serological subtypes. In the avian model, DNA expression vectors for the H7 subtype (comprising a DNA transcription unit encoding the H7 subtype hemagglutinin) have been used to provide protection against challenge with an H7N7 virus. In the murine model, a DNA transcription unit expressing the H1 hemagglutinin was used to immunize against an H1 N1 virus.

4

EXAMPLE 1

Immunization Of Chickens Against Influenza Virus

Figure 2:
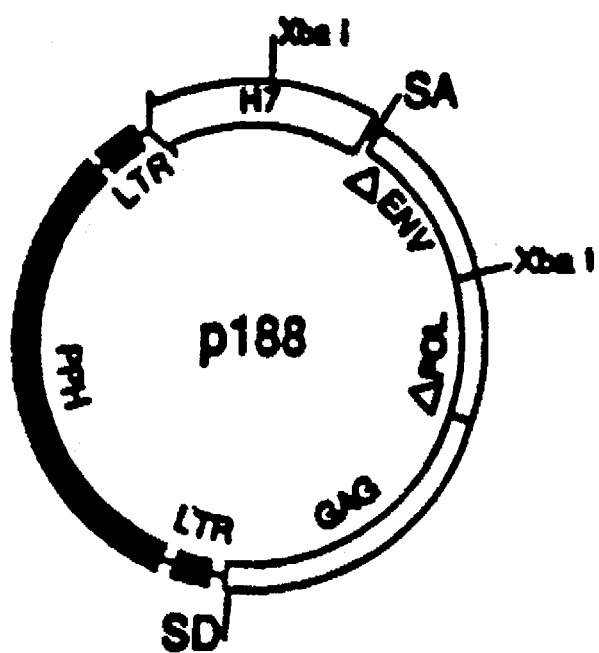
FIG. 2 is an illustration of a bacterial plasmid containing a DNA transcription unit (p188) comprising an influenza virus hemagglutinin type 7(H7) gene expressed by a replication defective retroviral vector.
Figure 3:
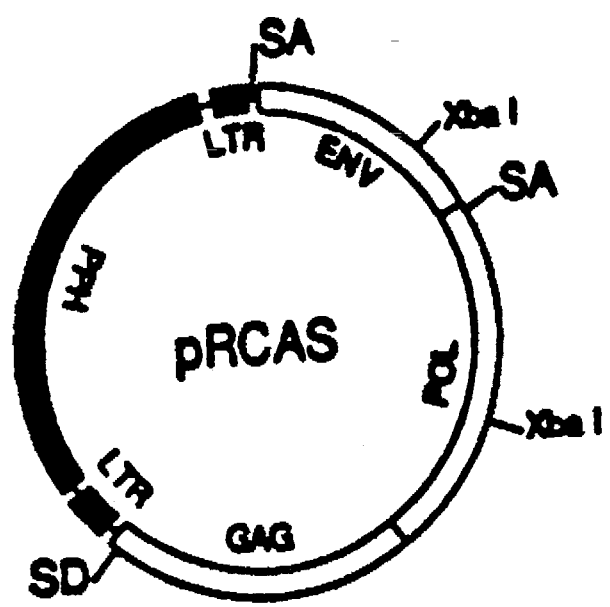
FIG. 3 is an illustration of a bacterial plasmid comprising a retroviral vector (pRCAS) with no H7 insert, used as a control.

Procedure:

A DNA transcription unit referred to as pP1/H7(FIG. 1), encoding a replication competent avian leukosis virus expressing the influenza virus hemagglutinin type 7(H7) gene was constructed as described in Hunt et al., *J. of Virology*, 62(8):3014–3019(1988). DNA unit p188(FIG. 2) encoding a replication defective derivative of pP1/H7 that expresses H7 but is defective for the avian virus vector polymerase and envelope proteins was constructed by deleting an XbaI fragment from pP1/H7. DNA unit pRCAS (FIG. 3), encoding the avian leukosis virus vector, with no influenza virus insert, was constructed as described in Hughes et al., *J. of Virology*, 61:3004 (1987). DNA units were diluted in saline at a concentration of 100 µg per 0.2 ml for inoculation.

To test the ability of the inoculated DNA to protect against a lethal influenza virus challenge, groups of three-week old chicks were inoculated with pP1/H7, p188, or pRCAS DNA. Specific pathogen free chicks that are maintained as an avian-leukosis virus-free flock (SPAFAS, Norwich, Conn.) were used for inoculations. Each chick received 100 µg of DNA ($\sim 1\times 10^{13}$ molecules) intravenously (iv), 100 µg intraperitoneally (ip), and 100 µg subcutaneously (sc). Four weeks later chicks were bled and boosted with 300 µg of DNA (100 µg iv, 100 µg ip, and 100 µg sc). At one week post-boost, chicks were bled and challenged by the nares with 100 lethal doses ($1\times 10^4$ egg infectious doses) of a highly pathogenic type H7 avian influenza virus, A/Chicken/Victoria/1/85(H7 N7) (Ck/Vic/85). The chickens were observed daily for ten days for signs of disease. One and one half weeks after challenge, sera were obtained from surviving birds. These as well as the pre- and post-boost sera were used for analyses for hemagglutination inhibiting antibodies (HI).

Sera were analyzed in microtiter plates with receptor-destroying enzyme-treated sera as described by Palmer et al., *Advanced Laboratory Techniques for Influenza Diagnosis*, p. 51–52, Immunology series no. 6, U.S. Department of Health, Education, and Welfare, Washington, D.C. (1975).

Results:

The H7-expressing DNA transcription units protected each of the chickens inoculated with pP1/H7 or p188(Table 1). In contrast, inoculation with the control DNA, pRCAS, failed to protect the chickens against lethal virus challenge. The birds in the control group started to show signs of disease on the second day post-challenge. By the third day, three of the six control birds had died and all control birds were dead by the fifth day. The birds inoculated with hemagglutinin-expressing DNAs showed no signs of disease. By one and one half weeks post challenge both of these groups had developed high levels of HI antibody.

EXAMPLE 2

Immunization Against Influenza Virus is Reproducible

To assess the reproducibility of the protection elicited by immunization with the replication-defective H7-expressing DNA, the experiment described in Example 1 was repeated three times using only p188 and pRCAS DNAs for inoculations. The results of the repeat experiments confirmed that the H7-expressing p188 DNA could afford protection against a lethal challenge (Table 2). In contrast to the first experiment, in which all of the p188-inoculated chickens survived the lethal challenge, immunizations in the 2 nd, 3 rd, and 4 th experiments achieved only partial protection with from 28% to 83% of the vaccinated birds surviving. Further, in contrast to the first experiment in which vaccinated birds showed no signs of disease, most of the survivors of the repeat experiments showed transient signs of post-challenge sickness. As in the first experiment, the control DNA did not provide protection. Summing the results of the 4 experiments, 28 out of 56 p188-vaccinated birds survived whereas only 1 of 55 control DNA-inoculated birds survived. Thus, despite the variability, significant immunization was achieved.

EXAMPLE 3

Immunization can be Accomplished by Several Different Routes of Inoculation

Figure 4A:
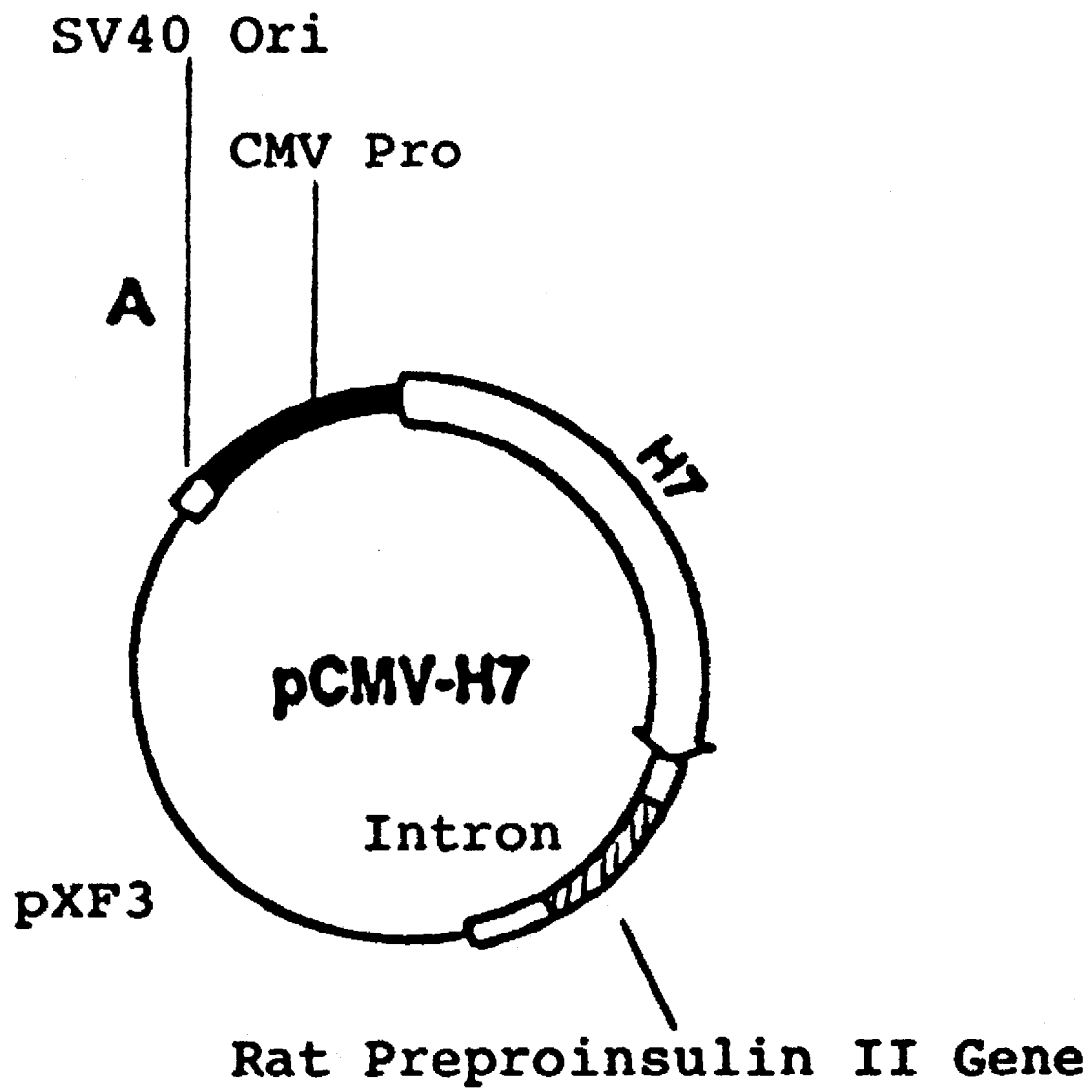
FIG. 4A is a schematic representation of the nonretroviral vector comprising the influenza virus antigen DNA transcription unit encoding subtype H7 hemagglutinin.
Figure 4B:
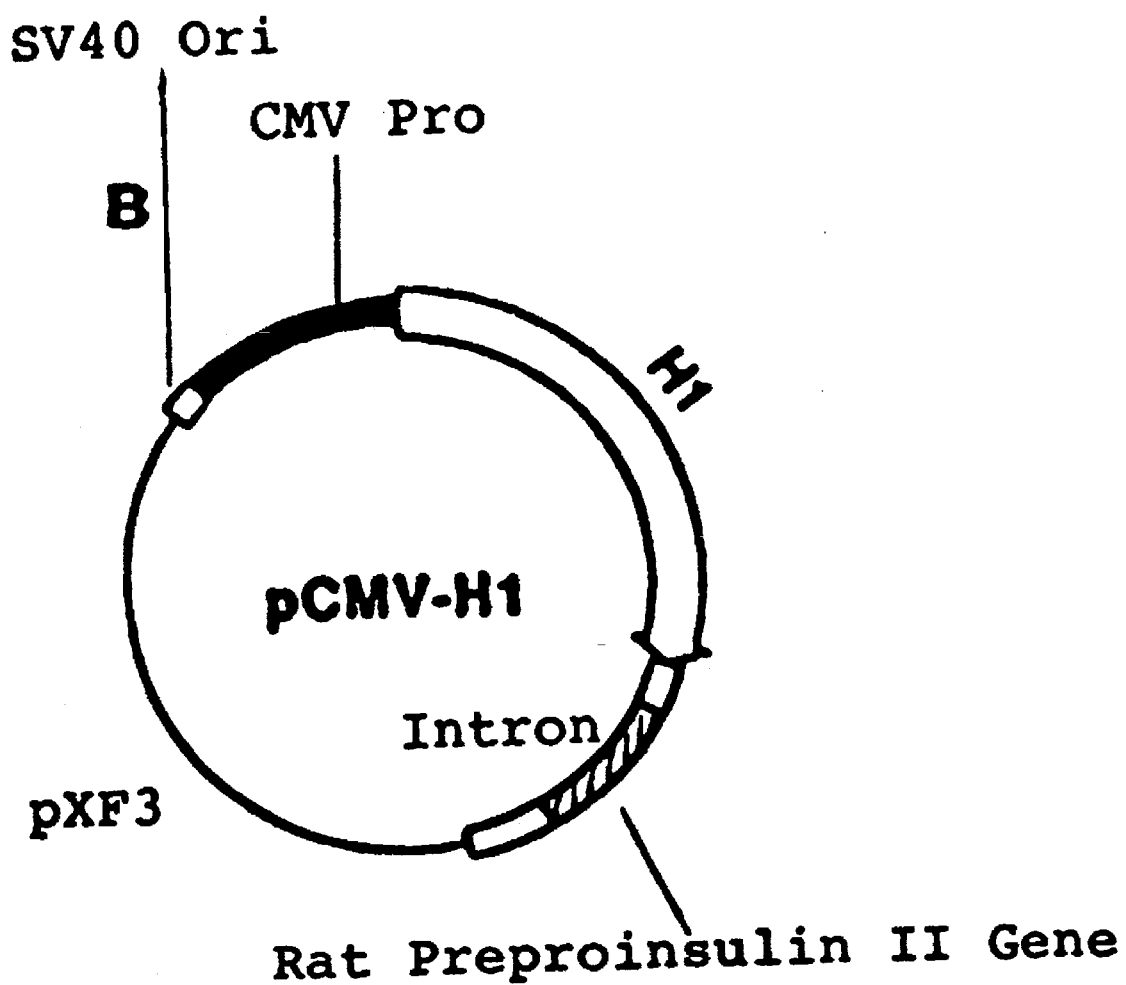
FIG. 4B is a schematic representation of the nonretroviral vector comprising the influenza virus antigen DNA transcription unit encoding subtype H1 hemagglutinin.

Procedure:

The DNA encoding p188-H7 and control DNA were tested again for the ability to protect against a lethal influenza virus challenge. This experiment included a group that was vaccinated and boosted by three routes of inoculation (i.e., ip, iv and sc), a group that was vaccinated by the same three routes but did not receive a boost, small groups that were vaccinated and boosted by only one route of inoculation and a control group treated with the anti-influenza virus drug, amantadine-HCL. This last group was included to allow the comparison of antibody responses to the challenge virus in vaccinated and unvaccinated chickens. The amantadine-treated birds were given 0.01% amantadine in their drinking water beginning 8 hours after challenge and were also injected ip with 1.0 ml of 0.1% amantadine 24 and 48 hours after challenge.

Results:

The results of this experiment confirmed that the replication defective H7-expressing DNA (p188) could afford protection against a lethal virus challenge (Table 3). The p188 immunized birds showed transient signs of sickness following the challenge. As in the previous experiments, the control DNA did not provide protection. All of the 5 amantadine-treated control birds developed disease. Four of these survived the challenge, providing sera that could be used to compare the time course and specificity of anti-influenza virus responses in immunized and non-immunized chickens (see Example 5 below).

EXAMPLE 4

Immunization can be Accomplished by Several Different Routes of Inoculation

Procedure:

A third experiment was initiated to increase the numbers of birds in the test groups and to further evaluate the efficacy of different routes of immunization. In this experiment 12 chicks were inoculated with 100 μg p188 by the iv, ip, and sc routes, 8 chicks were inoculated iv-only and 8 ip-only. For controls, 12 chicks were inoculated with pRCAS and 12 chicks were not inoculated. All immunizations were followed by a boost four weeks after the initial inoculation. The boosts used the same DNA dose and sites of inoculation as the vaccinations. The control and immunized animals were challenged with ck/vic/85 1–2 weeks after the boost, with high challenge doses used in order to achieve essentially 100% killing within 1–2 weeks.

Results:

The results again demonstrated protection by p188 (Table 4). Eight of the 12 p188 immunized birds survived, whereas all 12 of the control pRCAS chickens died. The twelve birds in the untreated control group also had no survivors. Six out of the 8 chickens inoculated iv-only with p188 survived whereas none of the 8 chickens inoculated ip-only survived.

EXAMPLE 5

Analysis of Antibody Response to Challenge Virus in Vaccinated and Unvaccinated Animals Procedure:

To allow the comparison of antibody responses to the challenge virus in vaccinated and unvaccinated chickens, experiment 2 from Example 2(Table 2) included a non-vaccinated group rescued with the anti-influenza A virus drug, amantadine-HCL (Table 2) (Webster, R. G., et al., *J. Virol.*55:173–176(1985)). All of the 5 amantadine-treated birds developed disease. Four of these survived, providing sera that could be used to compare antibody responses in immunized and non-immunized chickens (Table 6).

Sera from p188 inoculated and amantadine treated birds in the second experiment were analyzed for the time course of antibody responses to H7 and to other influenza virus proteins (Table 6). Antibody responses to H7 were quantitated using hemagglutination inhibition as well as virus neutralization and enzyme-linked immunosorbent assays (ELISA) for antibody. Neutralizing antibody was determined in chick embryo fibroblast cultures with 200 $TCID_{50}$ of virus using cytopathology and hemagglutinin for detection of virus replication.

Results:

Analysis of the antibody responses in vaccinated and amantadine-rescued birds revealed that the p188-inoculations had primed an antibody response to H7 (Table 6). As in experiment 1(Table 1), DNA vaccination and boost induced only low titers of antibody to H7. However, within one week of challenge, the DNA-immunized group had high titers of HI and neutralizing activity for H7. These titers underwent little (if any) increase over the next week. Furthermore, most of the post-challenge antibody in the vaccinated birds was directed against H7. This specificity was shown by comparing ELISA antibody titers to H7 virus (the immunizing hemagglutinin type) and H5 virus (a hemagglutinin type to which the birds had not been exposed). The post-challenge sera contained 20-times higher titers of ELISA antibody for the H7 than the H5 virus (Table 6). By contrast, in the amantadine-rescued group, antibodies did not appear until two weeks post-challenge. Most of this response was not H7-specific. This was demonstrated by the post-challenge sera from the amantadine-rescued birds which had comparable titers of ELISA antibody for the H5 and the H7 influenza viruses (Table 6).

EXAMPLE 6

Immunization of chickens and Mice Using a Nonretroviral Transcription Unit

Procedure

This experiment was performed in order to demonstrate that DNA transcription units devoid of retroviral DNA could be successfully employed to generate a protective immune response in both chickens and mice according to the methods herein described. The vectors used in this experiment to vaccinate chicken and mice are shown in FIG. 4A–4C. FIG.

4A is a schematic representation of pCMV-H7, a plasmid capable of expressing the influenza virus H7 subtype hemagglutinin under the transcription control of a cytomegalovirus (CMV) immediate early promoter. FIG. 4B is a schematic showing pCMV-H1, a plasmid capable of expressing the influenza virus H1 subtype hemagglutinin under the control of a CMV immediate early promoter. This is the DNA transcription unit used in the mouse experiments. FIG. 4C shows pCMV, a control plasmid which is not capable of expressing influenza antigens. These plasmids are derivatives of the pBC12/CMV vector of Dr. Brian Cullen, Duke University, Durham, N.C.

In the chicken and mouse experiments using pCMV-H7 and pCMV-H1 DNAs (the nonretroviral-based DNA transcription units) to generate immune responses, 100 µg of DNA was inoculated intravenously, intraperitoneally, and intramuscularly. All vaccinations were followed by a boost 4 weeks later. The boosts used the same DNA dose and sites of inoculation as the vaccinations. Challenge was 1–2 weeks after the boost, with high challenge doses being used so as to achieve essentially 100% killing within 1–2 weeks.

Results:

In five chicken trials using a nonretrovirus-based vector for vaccination (pCMV-H7) (FIG. 4A), approximately 60% of the chickens were protected. In one mouse trial, six out of six vaccinated mice and only one out of six control mice survived. Thus, considerable protection has been achieved using nonretroviral DNA expression vectors (containing DNA transcription units encoding viral antigens) to vaccinate animals. See, for example, Table 5.

In the chicken experiments, protective responses were associated with the rapid appearance of H7-specific antibodies after challenge (Robinson et al., vaccine 11: 957–960, 1993). Sera contained low to undetectable levels of anti-H7 antibodies after vaccination and boost. The first mouse experiment was similar to the chicken experiments in that inoculated mice also had low titers of anti-hemagglutinin activity before challenge. However, as in the chicken experiments, high titers of antibody appeared after challenge. The vast majority of this antibody was IgG.

EXAMPLE 7

Immunization of Mice by Vaccination with a Nonretroviral Transcription Unit: Analysis of Various Routes of Inoculation Procedure:

A DNA transcription unit referred to as pCMV-H1 (described in FIG. 4B) was successfully used to immunize mice against a lethal challenge with mouse adapted A/PR/8/34 H1 N1 influenza virus. This transcription unit encodes an influenza type H1 hemagglutinin under the transcription regulation of a CMV immediate early promoter. The H1 influenza virus hemagglutinin gene used in this construct is described in more detail in Winters et al., Nature 292:72 (1981).

Figure 5:
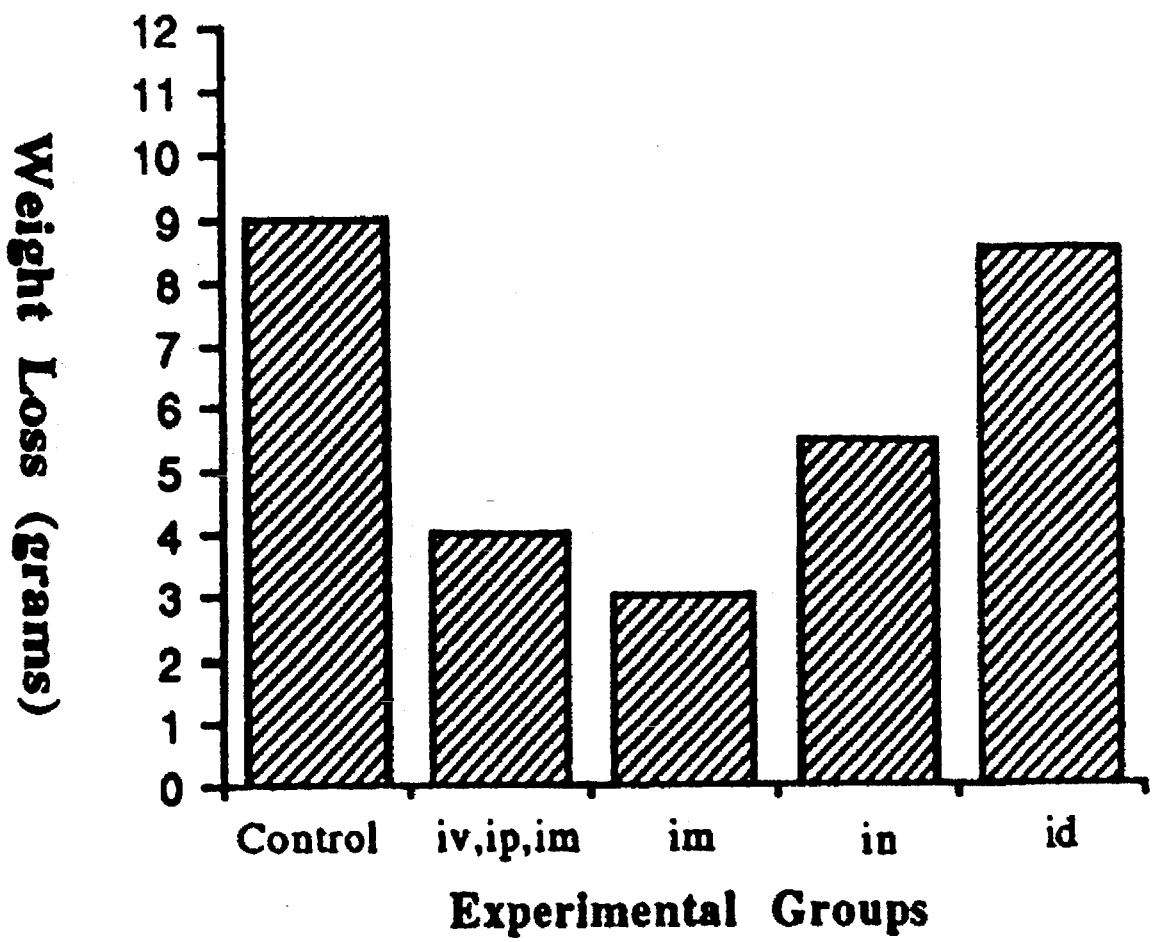
FIG. 5 is a bar graph depicting the maximum median weight loss for DNA-vaccinated mice in experiment 4, Table 7.

The first experiment was conducted by inoculation of 6–8 week old Balb/C mice with 100 µg of pCMV-H1 DNA by each of three routes; iv, ip and im. The second, third and fourth experiments each included one group of mice inoculated iv, ip and im, as well as additional groups representing different routes of inoculation (data summarized in Table 7 and FIG. 5.

The numbers in Table 7 represent the number of surviving mice/number of inoculated mice. The routes of inoculation (iv, intravenous; ip, intraperitoneal; im, intramuscular; sc., subcutaneous; in, intranasal; id, intradermal) for each trial are indicated. In most instances, 100 µg of DNA was administered per injection. Intramuscular (im) inoculations were given by injection of 100 µg DNA in each hip muscle. Intravenous (iv) inoculations were given by injection in the tail vein. Intranasal (in) administrations of DNA and challenges were done on Metofane-anesthetized animals (Pitman-Moore) (these animals inhale deeply). Intradermal (id) inoculations were done in the foot pad using only 50 µg of DNA. The control groups in experiments 2 and 3 received saline. The controls for experiment 1 received control DNA (vector without an insert encoding the antigen) administered iv, ip and im. The control group in experiment 4 received control DNA im, in and id. Occasional mice are resistant to influenza challenge. One of the survivors in the intranasal group in experiment 2, the one survivor in the control group in experiment 1, and 1 survivor in the control group in experiment 4 were such resistant mice. All groups showed signs of sickness following challenge. Data on weight loss were also collected and are presented in FIG. 5. The weight loss data provides a quantitative measure for the degree of sickness in the different experimental groups.

Results

The survival data, weight loss data and initial serology data from this series of experiments indicate that many routes of inoculation can provide protective immunity. In addition, these data demonstrate that intranasal inoculation (DNA nose drops administered to Metofane-anesthetized mice) can provide protective immunity to a lethal virus challenge. The method herein described may, therefore, provide means of stimulating mucosal immunity. (Table 7 and FIG. 5. Finally, these data demonstrate that some routes of inoculation are more effective than others for generating a protective immune response (Table 8).

EXAMPLE 8

Antibody Responses to Challenge Virus in Animals Vaccinated with a Nonretroviral DNA Transcription Unit Experiments analyzing the serum response in pCMV-H7 -vaccinated chickens were performed as described in Example 4. pCMV-H7 immunizations primed antibody responses, with high titers of antibody to H7 appearing post-challenge (Table 9).

TABLE 1

Protection Against Lethal H7N7 Influenza Virus with DNA Coding for H7 Hemagglutinin

| Group | Sick/Dead/Total | HI TITERS | | |
| --- | --- | --- | --- | --- |
| | | Post-vaccine 4 weeks | Post-boost 1 week | Post-Challenge 1.5 weeks |
| pP1/H7 | 0/0/6 | <.ᵃ | <. | 864 (160–1280) |
| p188 | 0/0/6 | <ᵇ | < | 427 (160–1280) |
| pRCAS | 6/6/6 | < | < | +ᶜ |

ᵃ(<.) means one of six birds had an HI titer of 10.
ᵇ(<) means that all birds had titers of less than 10.
ᶜ(+) means that all birds died.

TABLE 2

Reproducibility of Protection Against a Lethal H7 Virus
Challenge by Immunization with an H7-expressing DNA[a]

| Experiment | Fate of Challenge group (number of survivors/number tested) | | | |
|---|---|---|---|---|
| | p188 DNA | pRCAS DNA | Amantadine | No treatment |
| 1 | 6/6 | 0/6 | — | — |
| 2 | 5/6 | 1/5 | 4/5 | — |
| 3 | 9/32 | 0/32 | — | — |
| 4 | 8/12 | 0/12 | — | 0/12 |
| Total | 28/56 | 1/55 | 4/5 | 0/12 |

[a]Experiment 1 is the same as that presented in Table 1. Challenge was at one week post boost in experiment 1 and at two weeks post boost in experiments 2, 3 and 4, —, not tested.

Three-week-old SPAFAS chicks were inoculated with 100 μg of DNA by each of three routes (iv, ip and sc). Four weeks later, they were boosted by inoculation with 100 μg of DNA administered iv, ip and sc. One to two weeks later, chickens were challenged via the nares with 100 lethal doses of A/Ck/Vic/85 (H7N7).

Some survivors suffered transient signs of influenza virus infections.

TABLE 3

Protection Against Lethal H7N7 Influenza Virus
with DNA Coding for H7 Hemagglutinin

| Group | Route of Inoculation | Boost | Sick/Dead/Total[a] |
|---|---|---|---|
| p188 | ip/iv/sc | yes | 6/1/6 |
| p188 | iv only | yes | 1/1/2 |
| p188 | ip only | yes | 0/0/2 |
| p188 | sc only | yes | 2/2/2 |
| pRCAS | ip/iv/sc | yes | 5/4/5 |
| none | NA[b] | NA | |
| none Aman.[c] | NA | NA | 5/1/5 |
| p188 | iv/ip/sc | no | 4/4/6 |
| pRCAS | iv/ip/sc | no | 6/6/6 |

[a]Sick birds that survived developed only mild signs of sickness such as ruffled feathers and temporary loss of appetite.
[b](NA) not applicable.
[c](Aman.) is an abbreviation for Amantadine.

TABLE 4

Protection Against Lethal H7N7 Influenza Virus
with DNA Coding for H7 Hemagglutinin

| Group | Route of Inoculation | Boost | Sick/Dead/Total[a] |
|---|---|---|---|
| p188 | iv/ip/sc | yes | 6/4/12 |
| p188 | iv only | yes | 2/2/8 |
| p188 | ip only | yes | 8/8/8 |
| pRCAS | iv/ip/sc | yes | 12/12/12 |
| none | NA[b] | NA | 12/12/12 |

[a]Sick birds that survived developed only mild signs of sickness such as ruffled feathers and temporary loss of appetite.
[b](NA) not applicable

TABLE 5

Protection Against a Lethal H7 Influenza Virus
Challenge by Immunization with pCMV-H7 DNA.

| Trial | Fate of challenge group (number of survivors/number tested) | |
|---|---|---|
| | pCMV-H7 DNA | pCMV DNA |
| 1 | 5/6 | 0/6 |
| 2 | 4/6 | 0/6 |
| 3 | 2/6 | 0/7 |
| 4 | 4/6 | 1/7 |
| 5 | 4/6 | 0/7 |
| Total | 19/30 | 1/33 |

Immunization and boosts were the same as in Table 2. Some survivors developed transient signs of influenza-related illness.

TABLE 6

Antibody Response in H7-Immunized and Amantadine-Treated Birds

| Grp. | No.[a] | Bleed | HI | Antibody to Ck/Vic/85 (H7N7) Neutralizing | ELISA (×10$^{-3}$) | Antibody to Ck/Penn/1370/83 (H5N2) ELISA (×10$^{-3}$) |
|---|---|---|---|---|---|---|
| p188 | 6 | 1 wk PB[b] | 5 (0–10) | 2 (0–10) | 2 (0–10) | < |
| | 6 | 2 wk PB | 8 (0–20) | 13 (0–33) | 5 (0–10) | < |
| | 5 | 1 wk PC[c] | 112 (80–160) | 873 (33–3333) | 640 (100–1000) | 26 (0–100) |
| | 5 | 2 wk PC | 272 (80–640) | 540 (33–1000) | 640 (100–1000) | 46 |
| None Aman | 5 | 1 wk PB | <[d] | | < | < |
| | 5 | 2 wk PB | < | < | < | < |

TABLE 6-continued

Antibody Response in H7-Immunized and Amantadine-Treated Birds

| Grp. | No.[a] | Bleed | HI | Antibody to Ck/Vic/85 (H7N7) Neutralizing | ELISA (×10$^{-3}$) | Antibody to Ck/Penn/1370/83 (H5N2) ELISA (×10$^{-3}$) |
|---|---|---|---|---|---|---|
| | 4 | 1 wk PC | < | < | < | |
| | 4 | 2 wk PC | 300 (80–640) | 442 (100–1000) | 1000 (1000) | 1000 (1000) |

Antibody titers are given as the median (range).
[a](No.) Number of chicks in group at time of bleed.
[b](wk PB) means weeks post boost.
[c](wk PC) means weeks post challenge.
[d](<) means all birds had titers of less than 10.

TABLE 7

Survival Data for Four DNA Immunization Trials using pCMV-H1 in the Murine/Influenza Virus Model

| Trial | Control | iv, ip, im, | im | in | iv | id | sc | ip |
|---|---|---|---|---|---|---|---|---|
| exp 1 | 1/6 | 6/6 | | | | | | |
| exp 2 | 0/6 | 6/6 | 5/6 | 6/6 | 4/6 | | 4/6 | 0/6 |
| exp 3 | 0/6 | 6/6 | 6/6 | 3/6 | 6/6 | 6/6 | | |
| exp 4 | 2/6 | 3/4 | 7/7 | 4/5 | | 3/6 | | |
| Total | 3/24 | 21/22 | 18/19 | 13/17 | 10/12 | 9/12 | 4/6 | 0/6 |

TABLE 8

HI Antibody Titers Following Inoculation of PCMV-H1

| Time of bleed | Trial | Control | iv, ip, im, | im | in | iv | id | sc |
|---|---|---|---|---|---|---|---|---|
| Prebleed | 1 | < | < | | | | | |
| | 2 | < | < | < | < | < | | < |
| | 3 | < | < | < | < | < | < | |
| | 4 | < | < | < | < | | < | |
| 4 wk PV (preboost) | 1 | < | < | | | | | |
| | 2 | < | < | < | < | < | | < |
| | 3 | < | 40 | < | < | < | < | |
| | 4 | < | < | < | < | | < | |
| 10 da PB (pre-challenge) | 1 | < | < | | | | | |
| | 2 | < | 40 | < | < | < | | < |
| | 3 | < | 80 | < | < | 40 | < | |
| | 4 | < | < | 40 | < | | < | |
| 4–5 da PC | 1 | | | | | | | |
| | 2 | | | | | | | |
| | 3 | < | 80 | < | < | 80 | < | < |
| | 4 | < | < | 40 | < | | < | |
| 14–19 da PC | 1 | d* | 2560 | | | | | |
| | 2 | d | 640 | 320 | 320 | 320 | | 640 |
| | 3 | d | 160 | 320 | 640 | 640 | 640 | |
| | 4 | d** | 640 | 640 | 640 | | 640 | |

Serology for trials reported in Table 7. Data is for pooled sera. Designations and titers are the same as those in Table 9 with the exception of: control; da, days.
*One surviving mouse had a titer of 80.
**Two surviving mice had titers of 320.

TABLE 9

Antibody Responses to the H7 Challenge Virus in pCMV-H7 and pCMV-control DNA inoculated chickens

| Time of bleed | Trial | Control-DNA-inoculated | | | CMV-H7-DNA-inoculated | | |
|---|---|---|---|---|---|---|---|
| | | HI | Neutralizing | ELISA ($\times 10^{-3}$) | HI | Neutralizing | ELISA ($\times 10^{-3}$) |
| 4 wk PV (preboost) | 2 | < | < | < | < | < | < |
| | 3 | < | < | < | < | < | < |
| | 4 | < | < | < | < | < | < |
| | 5 | < | < | < | 2.5 | < | < |
| 1 wk PB (pre-challenge) | 2 | < | < | < | < | < | < |
| | 3 | < | < | < | < | < | < |
| | 4 | < | < | < | 2.5 | < | 2.5 |
| | 5 | < | < | < | 2.5 | < | 2.5 |
| 2 wk PC | 2 | D | D | D | 60 | 33 | 765 |
| | 3 | D | D | D | 60 | 33 | 1000 |
| | 4 | D* | D* | D* | 100 | 33 | 775 |
| | 5 | D | D | D | 140 | 108 | 1000 |

Designations and titers are as in Table 3 except for: PV, post vaccination and D, dead.
*One control bird survived in this group. Its post challenge titers were HI, 80; Neutralizing antibody, 10; and ELISA, 100. Control birds did not receive DNA.

Equivalents

Those skilled in the art will recognize, or be able to ascertain, using no more than routine experimentation, many equivalents to the specific embodiments of the invention described herein. These and all other such equivalents are intended to be encompassed by the following claims.

We claim:

1. A method of immunizing a vertebrate against an infectious agent, said method comprising administering to a vertebrate a DNA transcription unit comprising DNA encoding a hemagglutinin of the infectious agent operatively linked to a promoter region, whereby the vertebrate is protected from disease caused by the infectious agent.

2. The method of claim 1, wherein the DNA transcription unit is of nonretroviral origin.

3. The method of claim 1, wherein the infectious agent is a virus.

4. The method of claim 2, wherein the vertebrate is a mammal.

5. The method of claim 4, wherein the mammal is a human.

6. The method of claim 2, wherein the DNA transcription unit, in a physiologically acceptable carrier, is administered to a vertebrate through a route of administration chosen from the group consisting of intranasal, intravenous, intramuscular, intraperitoneal, intradermal and subcutaneous.

7. The method of claim 2, wherein the DNA transcription unit is administered to a vertebrate by contacting the DNA transcription unit in a physiologically acceptable carrier with a mucosal surface of the vertebrate.

8. A method of immunizing a vertebrate against an infectious agent, said method comprising administering to a mucosal surface of a vertebrate a DNA transcription unit comprising DNA encoding a hemagglutinin of the infectious agent operatively linked to a promoter region, in a physiologically acceptable carrier, whereby the vertebrate is protected from disease caused by the infectious agent.

9. The method of claim 8, wherein the DNA transcription unit is of nonretroviral origin.

10. The method of claim 9, wherein the mucosal surface is a nasal mucosal surface.

11. The method of claim 9, wherein the infectious agent is a virus.

12. The method of claim 9, wherein the vertebrate is a mammal.

13. The method of claim 12, wherein the mammal is a human.

14. A method of immunizing a vertebrate against influenza virus, said method comprising administering to a vertebrate a DNA transcription unit comprising DNA encoding an influenza virus antigen operatively linked to a promoter region, whereby the vertebrate is protected from disease caused by influenza virus.

15. The method of claim 14, wherein the influenza virus antigen is hemagglutinin.

16. The method of claim 15, wherein the hemagglutinin is subtype H1 or H7.

17. A method of immunizing a vertebrate against influenza virus, said method comprising administering to a mucosal surface of a vertebrate a DNA transcription unit comprising DNA encoding an influenza virus antigen operatively linked to a promoter region, in a physiologically acceptable carrier, whereby the vertebrate is protected from disease caused by influenza virus.

18. The method of claim 17, wherein the influenza virus antigen is hemagglutinin.

19. The method of claim 18, wherein the hemagglutinin is subtype H1 or H7.

* * * * *